United States Patent [19]
Hansen

[11] Patent Number: 5,427,906
[45] Date of Patent: Jun. 27, 1995

[54] SYSTEM FOR BRACING DENTAL IMPLANTS OR NATURAL TOOTH ROOTS TO SECURE ARTIFICIAL TEETH

[76] Inventor: Gorm P. Hansen, 1501 SE. 23rd Ave., Pompano Beach, Fla. 33062

[21] Appl. No.: 67,801

[22] Filed: May 27, 1993

[51] Int. Cl.⁶ .............................................. A61C 8/00
[52] U.S. Cl. .................................................... 433/173
[58] Field of Search ............... 433/172, 173, 174, 175, 433/176, 181, 182

[56] References Cited

U.S. PATENT DOCUMENTS

| | | | |
|---|---|---|---|
| 1,367,885 | 2/1921 | Means | 433/172 X |
| 3,514,858 | 6/1970 | Silverman. | |
| 3,748,739 | 7/1973 | Thibert | 433/173 |
| 4,085,506 | 4/1978 | Lew | 433/172 |
| 4,516,937 | 5/1985 | Bosker | 433/173 |
| 4,531,917 | 7/1985 | Linkow et al. | 433/176 |
| 4,713,003 | 12/1987 | Symington et al. | 433/173 |
| 4,722,688 | 2/1988 | Lonca | 433/173 |
| 4,738,619 | 4/1988 | Ross | 433/72 |
| 5,030,095 | 7/1991 | Niznick | 433/174 X |
| 5,052,928 | 10/1991 | Andersson | 433/172 |
| 5,082,442 | 1/1992 | Rosen | 433/17 |
| 5,125,840 | 6/1992 | Durr et al. | 433/173 |
| 5,195,892 | 3/1993 | Gersberg | 433/173 |
| 5,205,746 | 4/1993 | Chanavaz | 433/174 |
| 5,219,286 | 6/1993 | Hader | 433/172 |
| 5,246,369 | 9/1993 | Poulmaire | 433/173 |

Primary Examiner—Nicholas D. Lucchesi
Attorney, Agent, or Firm—Diller, Ramik & Wight

[57] ABSTRACT

A system for bracing dental implants or natural tooth roots to secure artificial teeth includes a plurality of implant members which are implanted in the jawbone or tooth roots of a patient and each has separately connected thereto or formed integral therewith an implant head having a recess for receiving a bar to which a denture can be removably secured.

27 Claims, 5 Drawing Sheets

SYSTEM FOR BRACING DENTAL IMPLANTS OR NATURAL TOOTH ROOTS TO SECURE ARTIFICIAL TEETH

BACKGROUND OF THE INVENTION

The invention is directed to a system for bracing dental implants or natural tooth roots to secure artificial teeth and an implantation method associated therewith.

A common implant system utilizes a bar which is secured to implant heads by screw-retained sockets. Clips or riders carried by a denture snap-secure the denture to the bar to allow the denture to be snapped in and out of a patient's mouth. U.S. Pat. No. 4,516,937 in the name of Hans Bosker is exemplary of this type of implant system.

U.S. Pat. No. 3,514,858 in the name of Ralph Silverman discloses another implant system in which a plurality of implant screws have releasably snap-secured thereto cap members which are bridged by a metal rod or bar. Several teeth of the denture are hollowed to conform to and seat upon the cap members thereby holding the denture in place in a patient's mouth.

U.S. Pat. No. 4,713,003 in the name of John M. Symington et al. discloses a dental implant for connecting an artificial tooth or a dental bridge to a person's jaw. The dental implant includes a tapered threaded implant body, an abutment or head keyed nonrotatably thereto, a connecting screw for coupling the implant body to the head and a retaining screw. A single tooth or a plurality of teeth can be anchored in the jaw of a patient by snapping recesses in the tooth or denture upon the implant abutment or head. In the case of a plurality of artificial teeth forming the denture, the complement of teeth are secured to each other in an integral fashion through a metal framework which is then connected to the abutment or head by a retaining screw which is inserted into the head through a bore of the associated artificial tooth. The bore in each tooth so affixed to the rod or metal framework is then filled with a plastic to provide a suitable surface on the tooth.

Other typical dental implants and associated accessories are far too numerous to describe in detail, but further typical examples can be found in the following U.S. patents and the patents cited therein, namely, Philippe Lonca (U.S. Pat. No. 4,722,688), David B. Rosen (U.S. Pat. No. 5,082,442), Stanley E. Ross (U.S. Pat. No. 4,738,619) and Leonard I. Linkow (U.S. Pat. No. 4,531,917).

SUMMARY OF THE INVENTION

Pursuant to the present invention, a novel dental implant system is provided which is less time consuming, less laborious, and less expensive than conventional implant systems. Custom laboratory design/fabrication is essentially eliminated because a novel implant head which is constructed to precision mate with both the implant, implant member, or tooth root on the one hand and a denture retention bar on the other which carries conventional clips or riders. The implant heads are supplied in various axial lengths, and each includes a slot having a bottom portion of a convex curvature which assures precise location of the attachment bar relative to a patient's gingiva/gum. The different axial lengths/heights of the implant heads assures that the base or bottom portion of each slot of each implant head is precisely located along the crest of the gingiva/gum, irrespective of irregularities in the latter and, of course, different depths of implant of the individual implant members. In this fashion, the attachment bar or rod which is firmly seated in each slot of each implant head and is appropriately contoured to the gum and/or jaw line is located a precise minimal distance above the gingiva/gum (preferably 1 mm), and this assures accurate location of the denture and excellent underlying support therefor when the denture is subject to high forces/stresses during mastication/chewing. Thus, by selecting implant heads of precise heights and bending-/contouring the attachment bar at chairside, a dentist can effect implants, even nonparallel implants up to 25°, in a highly efficient and cost-effective manner.

With the above and other objects in view that will hereinafter appear, the nature of the invention will be more clearly understood by reference to the following detailed description, the appended claims and the several views illustrated in the accompanying drawings.

DESCRIPTION OF THE PREFERRED EMBODIMENTS

Figure 1:
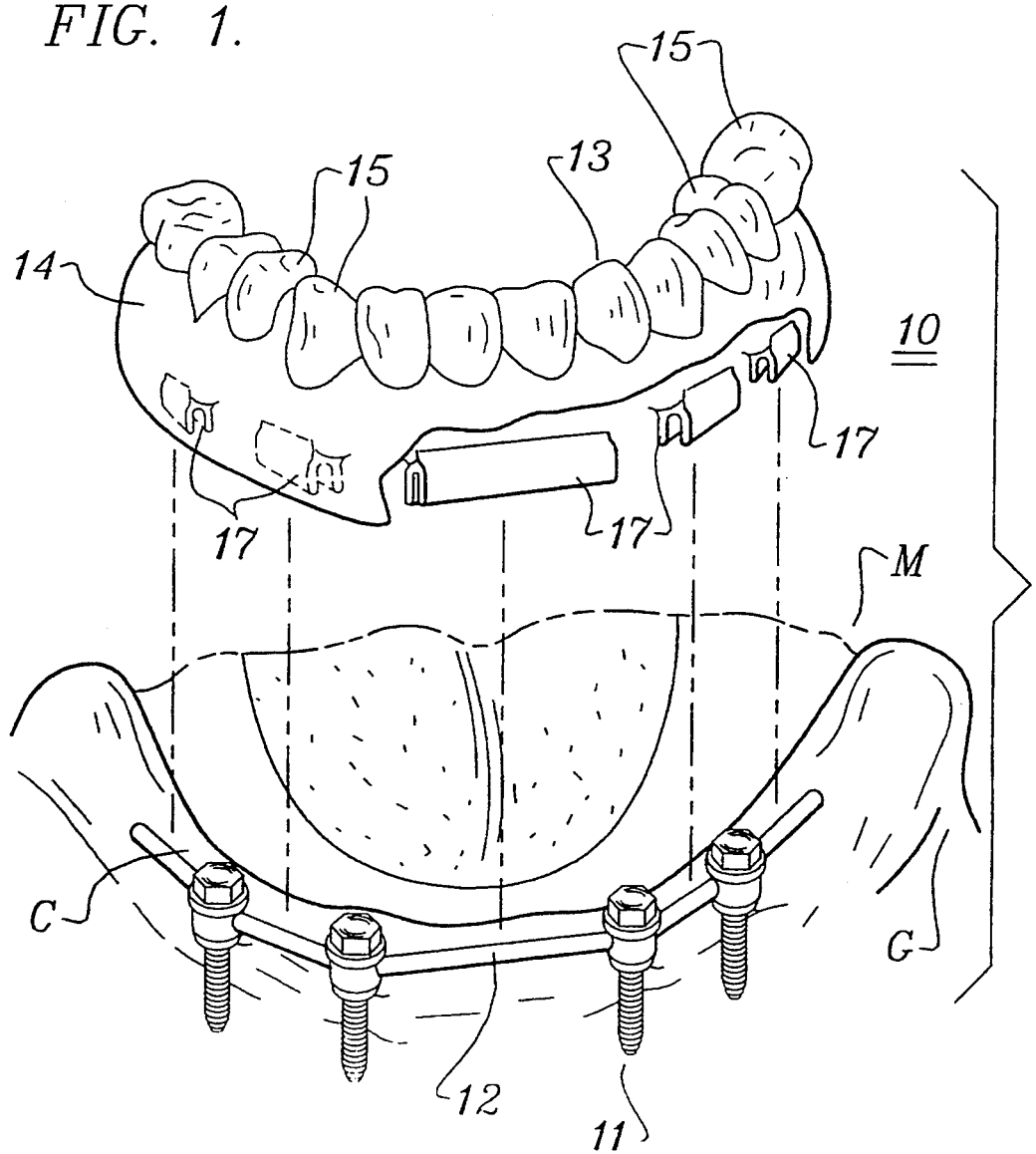
FIG. 1 is an exploded view of a novel dental implant system of the present invention, and illustrates a plurality of implants supporting an attachment bar and a denture carrying clips or riders for removably securing the denture to the attachment bar.

A novel dental implant system is fully illustrated in FIG. 1 of the drawings and is generally designated by the reference numeral 10. The dental implant system 10 includes a plurality of implants 11 between which and to which is secured an attachment bar or rod 12 and a denture 13 defined by a base support 14 carrying a plurality of teeth 15. The base support 14 has a concave undersurface 16 (FIG. 6) into which projects a plurality of resilient bifurcated generally C-shaped clips or riders 17.

Figure 2:
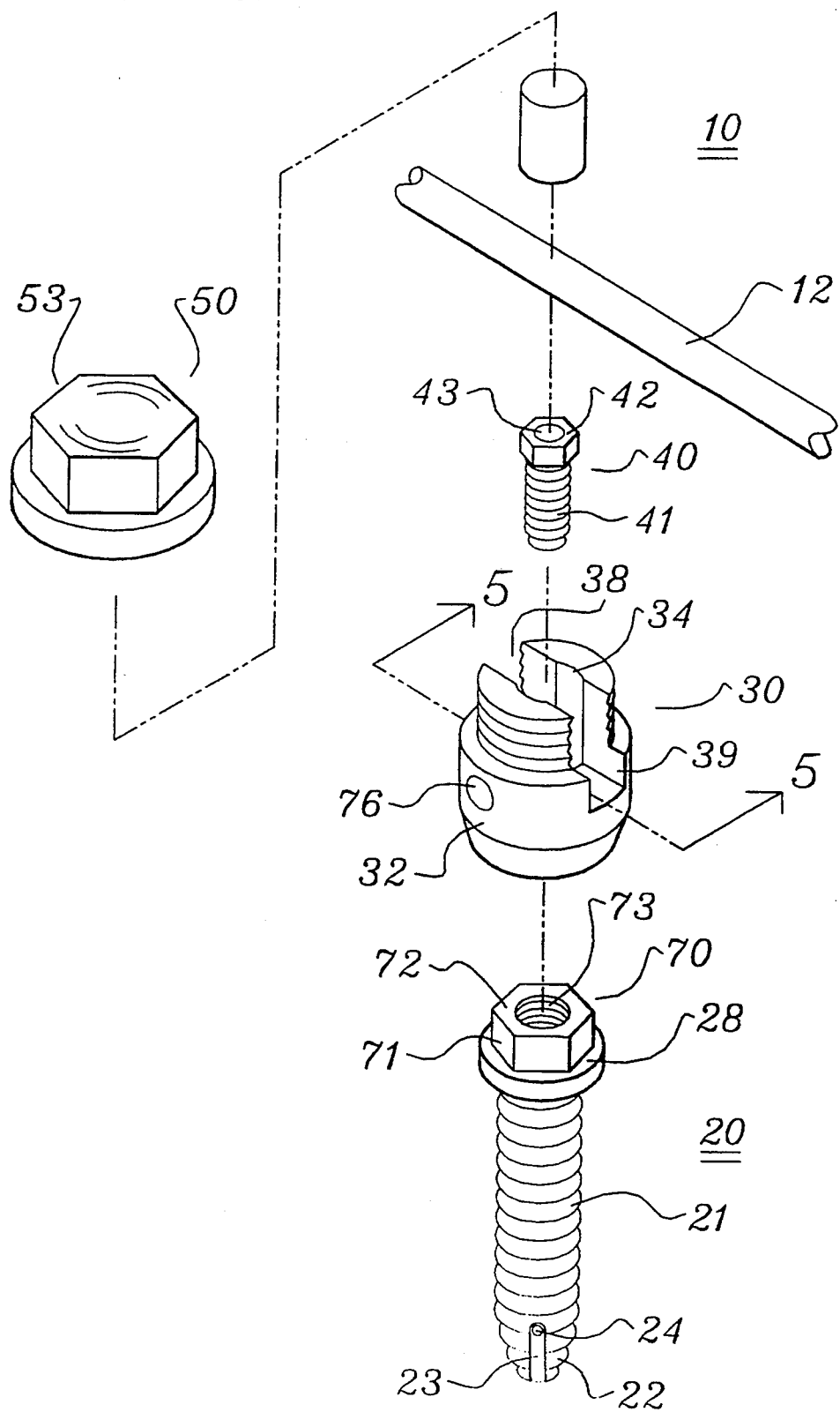
FIG. 2 is an enlarged perspective view of the system of FIG. 1, and illustrates a portion of the attachment bar and one of the implants of FIG. 1 which is defined by an implant member, an implant head, an implant head fastener and an attachment bar fastener.

In FIG. 1 the dental implant system 10 is shown associated with a lower mouth M of a patient or denture wearer and, as shown in both FIGS. 1 and 2, the mouth M includes a gingiva or gum G having an uppermost surface, crest or ridge C and an underlying jawbone J which, though not illustrated, includes an outermost hard bone layer and an inboard mesh bone layer. The base support 14 of the denture 13 essentially embraces the gingiva/gum G in the manner schematically illustrated in FIG. 6.

Figure 3:
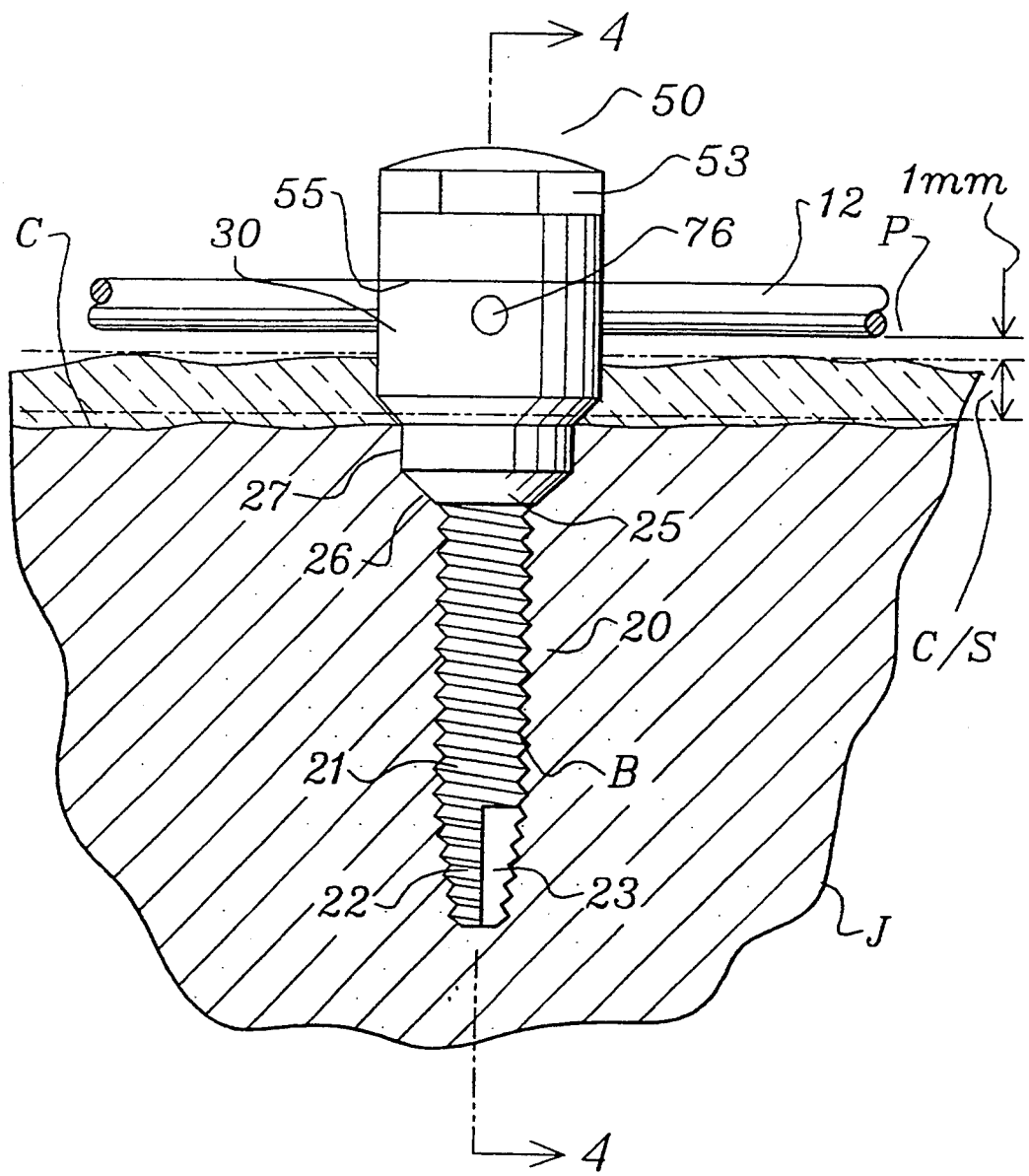
FIG. 3 is a fragmentary cross-sectional view of a jawbone and gingiva, and in side elevation illustrates one of the implants and the attachment bar supported thereby slightly above a ridge or crest of the gum.
Figure 4:
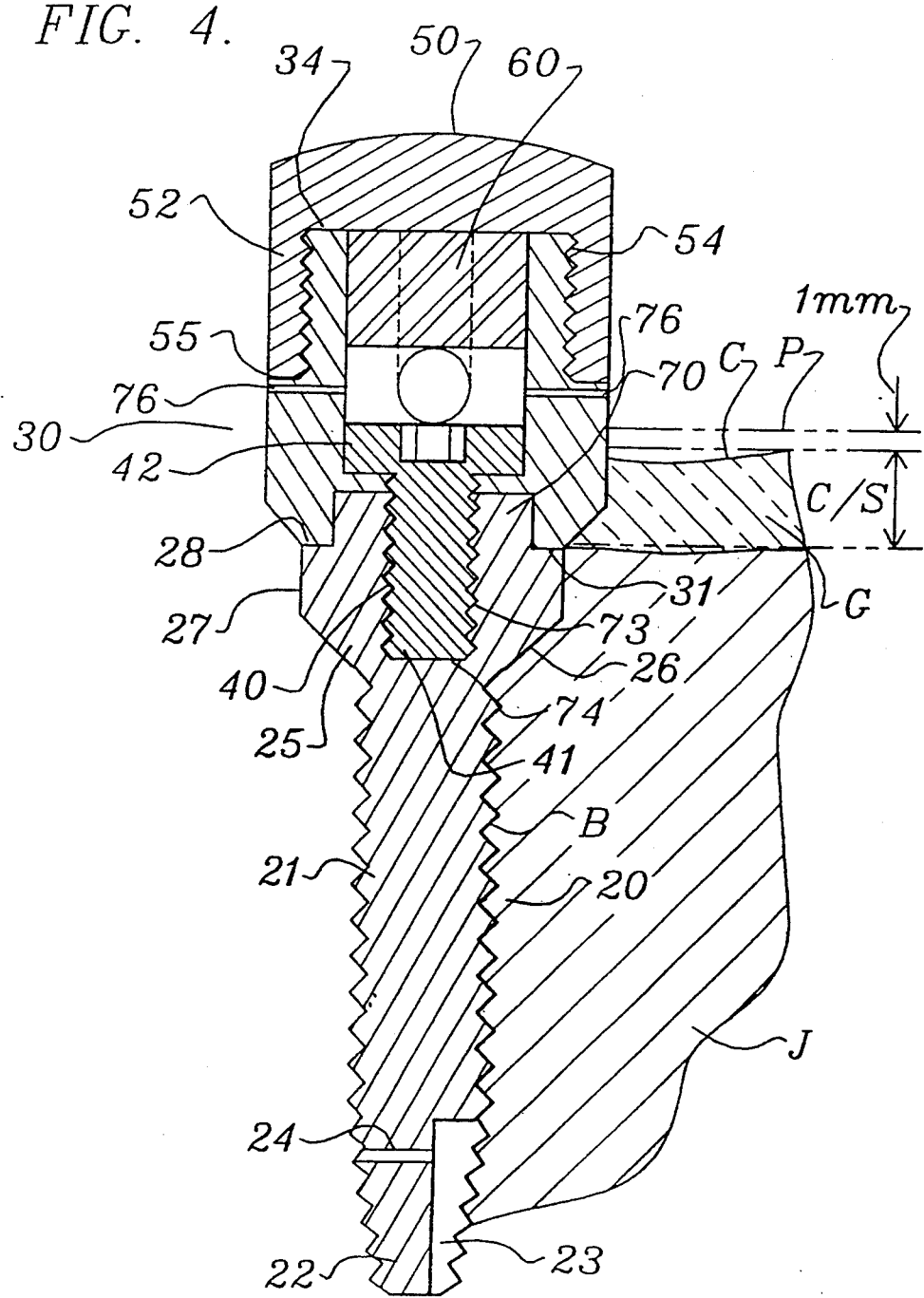
FIG. 4 is a slightly enlarged axially cross-sectional view taken generally along line 4—4 of FIG. 3, and illustrates components of the dental implant system in relative assembled relationship.
Figure 5:
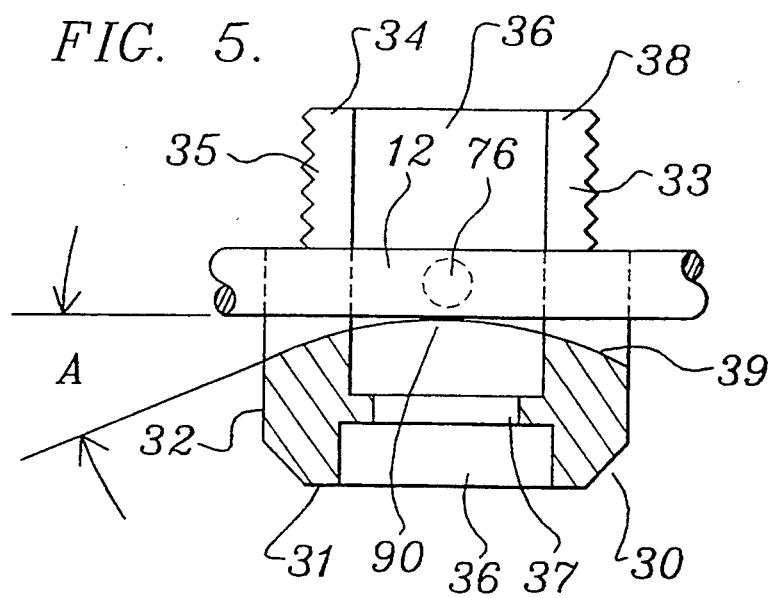
FIG. 5 is a cross-sectional view taken generally along line 5—5 of FIG. 2, and illustrates a convex bottom of a upwardly opening slot of the implant head upon which rests a portion of the attachment bar.

Reference is made specifically to FIGS. 2 through 5 of the drawings in which each of the implants 11 is shown defined by an implant member 20, and implant head 30, an implant head fastener 40, and attachment bar fastener 50, and an optional attachment bar gripping plug 60 (FIG. 4). The implant member 20, the implant head 30, the implant head fastener 40 and the attachment bar fastener 50 are all constructed from metallic material, such as a titanium alloy, a gold/platinum alloy or the: like while the attachment bar gripping plug 60 is a generally cylindrical piece of polyethylene or similar inert polymeric/copolymeric material.

The implant member or endodontic post 20 is essentially a cylindrical elongated post or stem having an external thread 21 along its length, including a conical tip portion or tip 22 thereof which includes a short channel 23 and a through opening 24. An upper end portion 25 (FIG. 4) of the implant member 20 is defined by a frusto-conical outer surface 26, a cylindrical surface 27, an annular shoulder 28 disposed normal to the central or longitudinal axis (unnumbered) of the implant member 20, and a hexagonal portion 70 projecting axially upwardly from the annular shoulder 28 and being defined by a plurality of flats 71 (FIG. 2). The hexagonal portion 70 includes an end face 72 through which opens a threaded bore 73 having a blind end 74. The external thread or threaded portion 21 of the implant member 20 is conventionally fastened/secured by the threads or serration within a bore B (FIGS. 3 and 4) formed in the jawbone J of a predetermined diameter and depth. An appropriate tool (not shown) is positioned upon the flats 71 of the hexagonal portions 70 of the implant member 20 to seat the same appropriately in the bore B. The depth of the implant member 20 is such as to maintain the distance from the annular shoulder 28 to the crest C of the gum G at an absolute minimum with this distance being designated by the reference character C/S in FIGS. 3 and 4. By maintaining the distance C/S at a minimum, the axial height of the head 30 associated therewith can also be held to a minimum which in turn assures that the denture 13 is positioned as intimately close to the crest C of the gum G (FIG. 6) as is possible when the clips 17 are secured to the attachment bar or rod 12, as will be described further hereinafter.

The implant head 30 is generally of a tubular configuration and includes a lower annular end face 31 defining an end of a relatively large lower cylindrical portion 32 and adjacent thereto an upper cylindrical end portion 33 having an upper annular end face 34. The upper cylindrical end portion 33 has an external thread 35. A central bore 36 extends between the end faces 31, 34 and is interrupted at the larger lower cylindrical end portion 32 by a radially inwardly directed annular shelf or rib 37. Recess means in the form of a generally upwardly opening U-shaped slot 38 is formed in the entirety of the upper cylindrical end portion 33 and partially in the larger lower cylindrical end portion 32 with a bottom portion or blind bottom end 39 (FIG. 5) of the slot 38 being of a generally upwardly convex configuration and setting-off an angle A of approximately 15° relative to the axis (unnumbered) of the attachment bar 12 seated thereupon. Diametrically opposite bores 76 (FIGS. 4 and 5) are formed in the larger cylindrical portion 32 for the receipt of a tool for holding the implant head 30 in any desired position incident to fixing such a position relative to the implant member 20 by tightening the implant head fastener 40, as will be described further hereinafter.

The implant head fastener 40 includes a threaded stem 41 which is complementary to the threaded bore 73 of the implant member 20 and has a cylindrical head 42 whose exterior diameter is slightly less than the diameter of the cylindrical bore 36 of the implant head 30. A polygonal blind recess or slot 43 is formed in the head 42 into which a tool, such as an Allan wrench or screwdriver, can be inserted for tightening or loosening the implant head fastener 40.

As is best illustrated in FIG. 4, the axial height of the implant head 30 is so selected that an apex or highest point of the convex bottom 39 (FIG. 5) is in a plane P (FIGS. 3 and 4) which is only very slightly above (1 mm) the crest C of the gum G. In other words, the distance C/S between the shoulder 28 and the crest C at the gum G is established by selecting an implant head 30 with an axial distance between its lower annular end face 31 and a crest 90 of the convex bottom 39 of the U-shaped slot 38 such as will position the lowest surface of the attachment bar 12 1 mm above the gum crest C, as is illustrated in FIGS. 3 and 4 of the drawings. This assures the intimate attachment of the denture 13 to the attachment bar 12, as earlier described and shown in FIG. 6.

As is most apparent from FIG. 1, since each patient's jaw J is distinctive, each of the implants 11 are positioned at different points along the jaw but because of the ability of selecting implant heads 30 of different heights, the attachment bar 12 will be located generally a constant 1 mm from the crest C at the gum G anywhere along the length of the gum G. Obviously, the implant heads 30 are necessarily first rotated relative to the implant members 20 and then locked in the desired positions by the implant head fasteners 40 to secure the attachment bar 12 to the jaw J. Also, the attachment bar 12 can be, of course, suitably bent, as shown in FIG. 1, so that portions thereof are readily positioned within each of the U-shaped slots 38.

After the attachment bar or rod 12 has been bent-/conformed as need be to seat properly in the slots 38 of the implant head 30, the relatively stiff, though somewhat resilient attachment bar gripping plug 60 (FIG. 4), is inserted into the cylindrical bore 36. The plug 60 is of an exterior cylindrical diameter corresponding generally to that of the bore 36 and the axial height of the plug 60 is slightly (1/10,000") greater than the distance between the uppermost surface of the attachment bar 12 when seated in the slot 38 in intimate engagement with the crest 90 of the bottom convex surface 39 and the upper end face 34 of the implant head 30. Stated otherwise, when the plug 60 is inserted in the bore 36, an upper edge portion thereof (unnumbered).projects axially upwardly above the upper annular end face 34 of the implant head 30 approximately 1/10,000". Thus, when a force is applied in the downward direction, as viewed in FIG. 4, by the securement of the attachment bar fastener 50 to the implant head 30, each portion of the attachment bar 12 within its associated U-shaped slot 38 will be brought into intimate bearing engagement with the crest 90 of the bottom convex surface 39 of the slot 38.

The attachment bar fastener 50 is simply a cap nut having an end wall (unnumbered) and a peripheral skirt 52 having exterior flats 53 and interior threads 54 which can be threaded upon the threads 35 of the implant head 30 in the manner clearly illustrated in FIG. 4.

The gripping plug 60 is optional and need not be necessarily utilized with any one or all of the implants 11 and, if eliminated, a lowermost annular face 55 of the peripheral skirt 52 will bear against an uppermost surface (unnumbered) of the attachment bar 12 to thereby force the same into clamping contact against and in association with the crest 90 of the bottom convex surface 39 of the U-shaped slot 38 of each of the implant heads 30, as is readily apparent from FIGS. 3 and 4 of the drawings.

Figure 6:
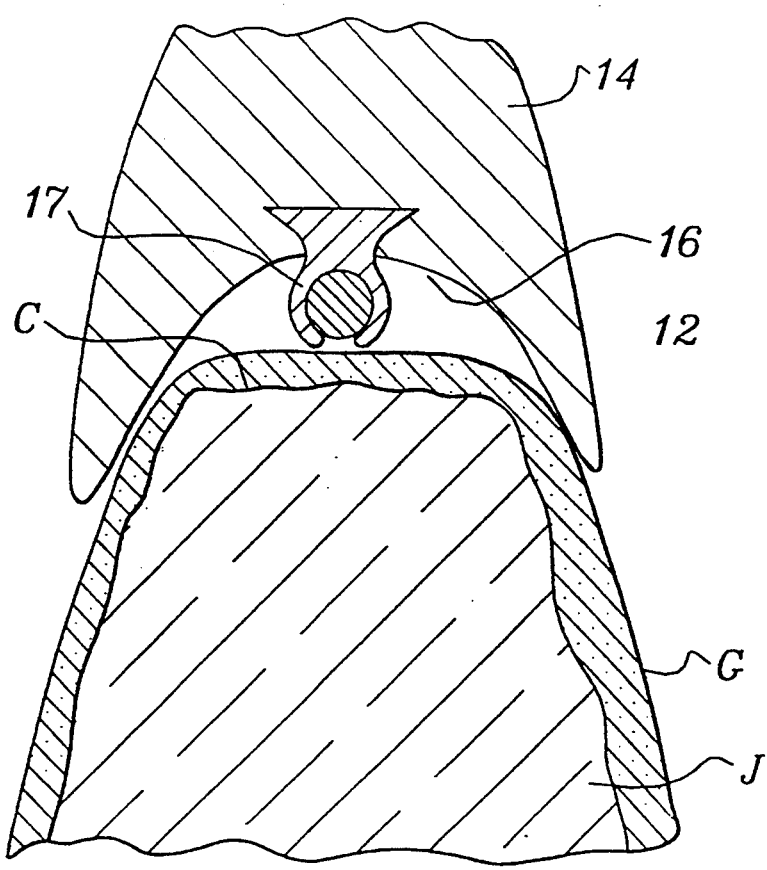
FIG. 6 is an enlarged fragmentary cross-sectional view through the denture and dental implant system of FIG. 1 after the two have been secured together, and illustrates the manner in which each of the clips or riders is snap secured to a portion of the attachment bar.

Once the attachment bar 12 is rigidly secured to each of the implants 11, as shown in FIG. 1, the denture 13 is simply snap-secured to the attachment bar 12 by the clips/riders 17, in the manner clearly illustrated in FIG. 6, and removal of the denture 13 is, obviously, equally readily effected by an upward lifting force applied thereto.

While the dental implant system 10 has been described with respect to the implants 11 being secured in the jawbone J of a patient, obviously, the implants 11 can be implanted in tooth roots by simply reducing the crown of the tooth to the gum line, utilizing a pilot drill and a counterbore drill to size the tooth roots to accept an implant member 20 of a particular length/height, post diameter and head diameter. Furthermore, since tooth roots vary in their angularity relative to the jawbone, it is within the scope of the present invention to provide implants in which the axis of the endodontic post 21 is other than coincident to the axis of the upper end portion 25 or the threaded bore 73 and can, for example, vary at angles ranging upwardly from 0° to and beyond 25°. Thus, if a particular tooth root and the pilot bore formed therein was disposed at 15° to the nominal horizontal plane of the gum crest C, an implant 11 would be selected in which the post 21 was offset by a like number of degrees (15°) from the upper end portion 25, and once implanted, the axis of the upper portion 25 and the implant head 30 secured thereto would be disposed generally normal to a horizontal plane through the nominal crest C of the gum G. Thus, by varying the angles of the upper end portions 25 of various implants 11 relative to the posts 21 thereof, all of the U-shaped slots 38 would open generally in a nominal vertical plane which would further assure accurate location of the attachment bar 12 and precision unification of the denture 13 relative thereto.

The implant member 20 is a preferred embodiment of the invention, but it is to be understood that the implant member is only one of a variety of different designs capable of being used with the implant head 30. There are a variety of different implant members 20 presently on the market and might, for example, be longer or shorter than that illustrated, can have a threaded exterior surface, etc. Furthermore, the implant member 20 and the implant head 30 can be of an integral one-piece construction in which case the implant head fastener 40 is, obviously, not required in those constructions in which the implant member 20 and the implant head 30 are of an integral one-piece construction, the implant member 20 and specifically the post 21 thereof is of a relatively small diameter so that the post 21 can be inserted into a tooth root. Furthermore, where the implant member 20 and the implant head 30 are of a one-piece integral construction, the axis of each can be coincident or can vary from 0° to and beyond 25° with the specific angle being selected such that the axis of the implant head 30 would be disposed generally normal to a horizontal plane through the nominal crest C of the gum G. As in the earlier example, if the tooth root and the pilot bore formed therein was disposed at 15° to the nominal horizontal plane of the gum crest C, the post 21 would be offset by 15° relative to the axis of its integral implant head 30. In addition, though the length of the post 21 can vary, be it separately connectable to or integral with the implant head 30, the post can be appropriately cut to length for insertion into a jaw or bored tooth root.

Although a preferred embodiment of the invention has been specifically illustrated and described herein, it is to be understood that minor variations may be made in the apparatus without departing from the spirit and scope of the invention, as defined in the appended claims.

I claim:

1. A dental implant system comprising a plurality of implant members each of which is adapted to be implanted in the jawbone of a patient, an implant head associated with each implant member, recess means associated with each implant head, a bar spanning said implant heads and being seated in each said recess means, means for securing said bar in seated relationship to each of said recess means, and means for removably securing a denture to said bar.

2. The dental implant system as defined in claim 1 including means for retaining each implant head relative to its implant member at any one of a plurality of different positions of relative rotation therebetween.

3. The dental implant system as defined in claim 1 wherein said recess means is a slot in each implant head.

4. The dental implant system as defined in claim 1 including means mounting each implant head for rotation about an axis of its associated implant member, and means for releasably locking each implant head with respect to its associated implant member in any selected position of relative rotation therebetween whereby said recess means can be appropriately positioned with respect to said bar.

5. The dental implant system as defined in claim 1 wherein each of said implant heads includes upper and lower end portions, said recess means is disposed in the upper end portion of each implant head, and said bar securing means includes a threaded securing member threaded upon each implant head.

6. The dental implant system as defined in claim 5 wherein said each implant head upper end portion includes an uppermost end face, and each of said recess means is a slot having a bottom portion and an open upper end portion opening through its associated uppermost end face.

7. The dental implant system as defined in claim 6 wherein each said threaded securing member bears against said bar and forces said bar into forceful engagement with the bottom portion of said slot of each implant head.

8. The dental implant system as defined in claim 7 wherein each said threaded securing member is a cap having an end wall and a peripheral skirt terminating in a terminal edge in bearing engagement with said bar.

9. The dental implant system as defined in claim 8 wherein each said cap peripheral wall and implant head are in complementary threaded engagement with each other.

10. The dental implant system as defined in claim 6 wherein each implant head upper end portion defines a chamber opening upwardly through its associated uppermost end face, a contact member in each of said chambers, and each threaded securing member bears against an associated contact member and forces said contact member into forceful engagement with said bar which is thereby brought into forceful engagement with the bottom portion of said slot of each implant head.

11. The dental implant system as defined in claim 5 including additional recess means in each implant head for receiving a tool to effect selected rotation of each head incident to locating the bar relative to said first-mentioned recess means.

12. The dental implant system as defined in claim 5 wherein each said threaded securing member bears against said bar and forces said bar into forceful engagement with each of said recess means.

13. The dental implant system as defined in claim 5 including means mounting each implant head for rotation about an axis of its associated implant member, and means for releasably locking each implant head with respect to its associated implant member in any selected position of relative rotation therebetween whereby said recess means can be appropriately positioned with respect to said bar.

14. The dental implant system as defined in claim 1 wherein each of said implant heads includes upper and lower end portions, said recess means is disposed in the upper end portion of each implant head, and said bar securing means includes a threaded securing member threaded upon each implant head upper end portion.

15. The dental implant system as defined in claim 1 wherein said recess means is an upwardly opening generally diametrically extending slot in each implant head.

16. The dental implant system as defined in claim 15 wherein said bar is a single piece of flexible material adapted to be generally permanently bent for accommodation relative to said slots.

17. The dental implant system as defined in claim 1 wherein said bar is a single piece of flexible material adapted to be generally permanently bent for accommodation relative to said recess means.

18. A method of creating a dental implant system to which a denture can be secured comprising the steps of providing at least two implant members each of which includes a rotatable implant head having an upwardly opening slot, implanting the at least two implant members at least partially within the jawbone or tooth roots of a patient, selectively rotating the rotatable implant heads to effect desired orientation of the slots relative to jaw contour, locking each oriented implant head, locating a denture attachment bar in spanning relationship between the implant heads and with portions of the denture attachment bar located in the upwardly opening slots, and securing each denture attachment bar portion to an associated head whereby a denture can thereafter be secured to said denture attachment bar.

19. The method of creating a dental implant system as defined in claim 18 including the step of forming bores in the jawbone or tooth roots prior to implantation, measuring the depth of each bore, and selecting a head of a height to position each head slot with a bottom portion thereof slightly above the gum crest of the patient.

20. The method of creating a dental implant system as defined in claim 19 including the step of bending the denture attachment bar to effect proper gum jawbone orientation prior to securing each denture attachment bar portion to its associated head.

21. The method of creating a dental implant system as defined in claim 18 including the step of bending the denture attachment bar to effect proper gum jawbone orientation prior to securing each denture attachment bar portion to its associated head.

22. An implant head comprising an implant body having upper and lower end portions each terminating in respective upper and lower terminal faces, said upper end portion including a peripheral face, a bore at least in said lower end portion and an upwardly opening slot in said upper end portion, said slot opening upwardly through said upper terminal face and diametrically oppositely through said peripheral face, said slot including a bottom, said bore opening through said slot bottom, and said upper and lower end portions being generally of a cylindrical configuration with said upper cylindrical portion being of a generally smaller diameter than said lower cylindrical portion.

23. The implant head as defined in claim 22 wherein said upper cylindrical portion carries thread means for threading thereto a complementary threaded attachment bar fastener.

24. The implant head as defined in claim 23 wherein said slot bottom is of a convex configuration.

25. The implant head as defined in claim 22 wherein said upper cylindrical portion includes said peripheral face.

26. An implant head comprising an implant body having upper and lower end portions each terminating in respective upper and lower terminal faces, said upper end portion including a peripheral face, a bore at least in said lower end portion and an upwardly opening slot in said upper end portion, said slot opening upwardly through said upper terminal face and diametrically oppositely through said peripheral face, said slot including a bottom, said bore opening through said slot bottom, and thread means defined by said implant body for threading thereto a complementary threaded attachment bar fastener.

27. The implant head as defined in claim 26 wherein said slot bottom is of a convex configuration.

* * * * *